United States Patent [19]

Marchosky et al.

[11] Patent Number: 4,719,919
[45] Date of Patent: Jan. 19, 1988

[54] IMPLANTABLE HYPERTHERMIA DEVICE AND SYSTEM

[75] Inventors: Jose A. Marchosky, Creve Couer; Robert B. Alek, Ellisville; Christopher Moran, Creve Coeur; Raymond E. Rutledge, Ballwin, all of Mo.

[73] Assignee: Ramm Associates, a partnership, Creve Coeur, Mo.

[21] Appl. No.: 697,697

[22] Filed: Feb. 4, 1985

Related U.S. Application Data

[63] Continuation of Ser. No. 459,708, Jan. 21, 1983, abandoned.

[51] Int. Cl.$^4$ .............................................. A61F 7/12
[52] U.S. Cl. ................................. 128/401; 128/303.1
[58] Field of Search ................ 128/303.1, 303.12, 399, 128/402, 736, 742, 419 PG, 784, 903, 401; 604/20

[56] References Cited

U.S. PATENT DOCUMENTS

| | | | |
|---|---|---|---|
| 2,777,445 | 1/1957 | Hart | 128/303.12 |
| 3,170,465 | 2/1965 | Henney et al. | 128/303.1 |
| 3,938,526 | 2/1976 | Anderson et al. | 128/303.1 |
| 3,942,535 | 3/1976 | Schulman | 128/419 PS |
| 3,949,388 | 4/1976 | Fuller | 128/903 |
| 4,046,139 | 9/1977 | Horn | 128/736 |
| 4,142,529 | 3/1979 | Latenser et al. | 128/303.12 |
| 4,146,029 | 3/1979 | Ellinwood | 128/419 P |
| 4,223,678 | 9/1980 | Langer et al. | 128/903 |
| 4,227,535 | 10/1980 | Connor | 128/401 |
| 4,232,679 | 11/1980 | Schulmen | 128/419 PG |
| 4,275,738 | 6/1981 | McDonald et al. | 128/419 PG |
| 4,312,364 | 1/1982 | Convert et al. | 128/804 |
| 4,331,161 | 5/1982 | Patel | 128/399 |
| 4,333,469 | 6/1982 | Jeffcoat et al. | 128/784 |
| 4,483,341 | 11/1984 | Witteles | 128/303.1 |

FOREIGN PATENT DOCUMENTS 0048402 of 1982 European Pat. Off. .......... 128/303.1

OTHER PUBLICATIONS

"An Experimental Method for Thermal Control of Heart Rate: Work in Progress", Parsonnet et al., Pace, Sep.-Oct. 1980.

"An Externally Programmable, Implantable, Integrated Cerebellar Stimulator", Murawski et al., IEEE Engr. in Med. & Biol. Soc. 1982.

(List continued on next page.)

Primary Examiner—William E. Kamm
Assistant Examiner—Max F. Hindenberg
Attorney, Agent, or Firm—Woodard, Emhardt, Naughton Moriarty & McNett

[57] ABSTRACT

A system for generating heat and sensing the temperature in an internal body organ such as in a tumor and for gaining information about the tumor for diagnosis and other purposes comprising a first system portion which is preferably entirely implantable beneath the skin of the person being treated or diagnosed including a probe device having electrical heater and sensor elements in it for implanting extending into the tumor to be treated and including an internal control unit also implantable under the skin and operatively connected to the heater and sensor elements in the probe, the internal control unit also including an electronic control unit for controlling the energizing of the heater element and having a sensor responsive portion responsive to the temperature sensed by the sensor element, and a transmitter/receiver device and a second system portion including an external control unit having a transmitter/receiver device for positioning on the skin adjacent to the internal transmitter/receiver device for exchanging information between the internal and the external control units, the external control unit also including a computer and associated computer control devices and software. The external control unit also includes system elements for controlling the application of electric energy to the heater element to generate heat in the body organ. The internal control unit may also include a rechargeable energy source rechargeable under control of the external control unit.

10 Claims, 9 Drawing Figures

OTHER PUBLICATIONS

"Brain Cancer Therapy Using an Implanted Microwave Radiator", Taylor, Microwave Journal, 1981.

Hornback, Ned B., *Hyperthermia and Cancer,* 1984, Chapter I, vol. II.

Storm, F. Kristian, "Hyperthermia in Cancer Therapy," 1983, Table of Contents.

Nussbaum, Gilbert H., "Physical Aspects of Hyperthermia", 1982, Table of Contents.

Sutton, Carl H., "Tumor Hyperthermia in the Treatment of Malignant Gliomas of the Brain," *Transactions of the American Neurological Association,* 96:195–199, 1971.

Anghileri, Leopold et al. [Eds.], *Hyperthermia in Cancer Treatment,* CRC Press, Inc., Boca Raton, Fla., 1986, pp. 26, 44, 126, 136–138.

IMPLANTABLE HYPERTHERMIA DEVICE AND SYSTEM

This is a continuation of co-pending application Ser. No. 459,708 filed on Jan. 21, 1983, now abandoned.

Malignant tumors and especially malignant brain tumors are one type of cancer that has a very poor cure rate. The available modalities of treatment, including surgery, radiation therapy, and chemotherapy, have not been of substantial success in most cases in the management of this disease. It is an established laboratory fact that altering the environment in which the tumor cells are developing can cause the death of the tumor, and modest increases in the temperature of the environment of tumor cells can lead to their destruction. It has also been proven by clinical research that a modest increase in the temperature of a tumor, known as hyperthermia technique, has led to regression, disappearance, and on some occasions, cure of malignant tumors. However, a system for delivering energy into the tumor environment to produce hyperthermia, especially for extended periods of time, is not presently available except for the use of radiation means which are damaging to the surrounding tissue and difficult to control. An ideal system for introducing hyperthermia should be efficient, accurate, reproducable, safe, programmable, and totally implantable or self contained under the skin of the patient for reasons that will become apparent.

The present invention teaches the construction and operation of a device and system that has all of the desirable characteristics mentioned above. For example, the present invention teaches the construction of an implantable probe connected electrically to an internal control unit (ICU), which probe and internal control unit and the connections therebetween are all implantable under the surface of the skin so that there is nothing that projects through or from the skin. In the present construction, the probe is an elongated member which includes one or more heater elements and one or more temperature sensors which are located on the probe at positions such that when the probe is implanted on the patient the heater and sensor elements will be positioned to heat and to respond to the tumor temperature at the locations desired to be treated. The heat sensors when properly located in relation to the tumor respond to and monitor the temperature of the tumor thereat, and the internal control unit is connected to the heater element or elements and to the sensors by wires which are preferably coil constructed and located under the skin so as to allow the patient normal body movement without discomfort and without the possibility for stretching or contracting the wires. It is also contemplated to use one or more probes each equipped with one or more heater elements and sensors all connected to be controlled by the same internal and external control means.

In the present construction, the internal or implanted control unit includes its own power supply which is implanted with the unit completely in the patient's body and under the skin. The power supply may include a battery or other energy source which is preferably rechargeable by external means that can be coupled to the internal means for this and other purposes. The power supply includes circuitry to deliver energy from the battery to the heater and sensor elements in the probe and also provides the energy for operating the internal control unit. The internal control unit controls the energizing and deenergizing of the heater element in response in part to the temperature sensed by the sensors and in part due to external and internal controls and programs and it includes means to control the amount of heat generated by the heater element and the frequency and duration that the heater element is energized. This is done under control of the sensors and other control and program means so that there is a careful and precise control over the amount of heat generated in the tumor according to a program established therefor. The device may include means for keeping an ongoing record of the operation for evaluation and reprogramming purposes and in some cases the same information may be used for diagnostic purposes. The internal control unit also contains means to store a program therefor, means to store responses of the sensors, and means for transmitting and receiving instructions to and from an external control unit and/or a computer so that information can be exchanged therebetween for evaluation and program updating. The information exchanged can be control information, information as to the amount of heat to be introduced into the tumor, information as to the temperature and changes in the temperature at specific locations in the tumor, information as to the charge remaining on the power supply, fail safe information, verification and assessment information, and information as to the frequency and duration of applied heat. This information can be stored in memory means which are included in the internal unit for transmission by internal transmission means through the skin to external receiver means which are part of the external control unit. The information thus exchanged can be used to program and reprogram the internal unit depending upon the amount and frequency of heat required to be generated taking into account the measured temperature of the tumor and the treatment requirements. The external control unit can also be used to control the recharging of the internal battery or power pack contained in the internal unit from time to time as required and to monitor the amount of power remaining in the power pack to assure continuity of operation of the internal unit and the safety of the patient. The external control unit, like the internal control unit, should also contain storage means for storing information it receives from the internal unit, and the external control unit should include computer means or means for coupling to a computer or other data processing device having the capability and software programs to evaluate the information it receives and to produce outputs for transmitting to and entering in the internal control unit as required. Such information can be used to reprogram the internal unit as by changing the amount and frequency of heat application to the tumor for some reason such as to achieve and maintain some desired tumor temperature. The computer to which the external unit is coupled should possess the software necessary to produce the functions described above.

So far as known there is no system in existence that has the features, benefits and capabilities of the present system including having means for predeterminately accurately generating heat in a tumor using a probe with a heater element thereon as distinguished from other forms of heat producing means such as radiation means which are known to often cause damage to tissue and organs adjacent to the area being treated when the radiation is applied to the tumor for therapeutic reasons. So far as known, there are no devices which include a self-contained implantable system for applying heat therapy to a tumor and which includes means to continuously monitor the temperature of the tumor in order to assess and verify the treatment and which are manually or automatically programmable to change or adjust the treatment. The present invention therefore represents a new, more accurate, and safer means for generating heat in a tumor or in some body organ without the use of medicines or radiation, for some therapeutic and/or other reason. The present invention allows for the internalization of a self contained control system which includes means programmable to control all of the functions thereof, and yet can be coupled to external control means for treatment evaluation, verification and assessment of past and present operational conditions and which can be programmed and reprogrammed to change the treatment as by selecting a different level of heat generation, a different schedule of treatment frequency and duration of heat application and which contains means for charging or trickle charging an internal power pack or battery to maintain and sustain the operating condition of the system and to substantially extend the life of the implanted system without surgical procedures. All of these and other functions can be performed on a continuing safe basis, for extended periods of time, and without having repeatedly to surgically remove portions of the implanted system.

The present system therefore represents an important advance in means for heat treating tumors and other body organs including particularly the treatment of brain tumors using carefully controlled and regulated hyperthermia means which do not produce any radiation which can cause damage to other body parts and functions, and the present system provides a useful additional medical option for use in treating such tumors. The present device also allows for prolonged periods of therapy under precisely controlled circumstances and with appropriate feedback and control systems which can be used to evaluate the results of the treatment and can be used to reprogram the system taking into account changes in the patient's condition and the condition of the tumor or other organ being treated. The present system also has fail-safe features which continuously monitor and, if necessary, update or abort the treatment so that the chances of putting the patient at risk are minimal.

It is an important advantage of the present invention that it provides a totally implantable hyperthermia system for the treatment of tumors and other internal organs and the like which substantially reduces the risk of infection even over prolonged periods of treatment by not having any parts of the implanted system pass through or extend from the skin. Also, since all of the operational components of the present system are implanted under the skin, a patient equipped with the implanted components may be ambulatory during treatment, and it is expected that at least some patients so equipped can be away from any external controls while treatment continues even for extended periods of time, often while carrying on other activities of daily living including possibly being involved in gainful employment. This is not usually possible with any other known hyperthermia or related treatment procedures. While the patient is moving about the treatment progresses under control of a program that is stored in the implanted system, and the program can be monitored and revised or changed from time to time as required by coupling the internal control unit to the external control means and if necessary to a central computer. As explained the power supply or battery that is incorporated into the implanted system is selected because it is small in size and rechargeable from external means as by trickle charging it by means which couple the internal and external units. The degree of flexibility and control available with the present system is non-existant in any known device at the present time. The present system therefore represents an important technical advance and a modality of management especially useful for the care and treatment of cancerous tumors which is not otherwise available on the market.

It is therefore a principal object of the present invention to provide an important alternative means for treating cancerous tumors.

Another object is to teach the construction and operation of an implantable system for controlling and monitoring the application of heat to an internal region of the body including into a cancerous tumor.

Another object is to provide means to control and program an implanted heat producing system by means which couple the implanted system to an external control system.

Another object is to provide a self contained implantable treatment system for use in generating heat in a cancerous tumor or other location inside the body to predeterminately raise and maintain a desired temperature in the tumor.

Another object is to provide the possibility for making patients with cancerous tumors including cancerous brain tumors ambulatory during treatment thereof.

Another object is to provide means for recharging a power supply implantable under the skin by means which couple to the implanted power supply from an external source through the skin.

Another object is to provide relatively safer means for treating cancerous tumors.

Another object is to generate heat in a tumor by means of an electric heater element positioned in the tumor.

Another object is to locate a heater element at a location within the tissue or tumor to be treated so that heat generated thereby radiates outwardly into the surrounding treatment area.

Another object is to minimize the surgical procedures necessary in the treatment of cancerous tumors including cancerous tumors located in the brain.

Another object is to provide an implantable system for applying heat to tumorous areas including means for regulating the amount, frequency and duration of heat applied in response at least in part to temperatures sensed by heat sensors also located in the region where the heat is applied.

Another object is to teach the construction and operation of a novel probe assembly capable of being implanted extending into a cancerous tumor with minimum surgical procedure and damage to the patient.

Another object is to minimize the surgical procedures necessary to implant and maintain a heat generating device in a tumor.

Another object is to provide more information for evaluation purposes during the treatment of tumors using a hyperthermia technique.

Another object is to provide a probe for extending into a cancerous tumor that includes means for generating heat in the tumor and means for sensing the tumor temperature at one or more locations in the region where the heat is generated.

These and other objects and advantages of the present invention will become apparent after considering the following detailed specification covering preferred embodiments thereof in conjunction with the accompanying drawings, wherein:

FIG. 1 is a side view of the head and upper body portion of a person equipped with an implanted hyperthermia system constructed according to the teachings of the present invention;

FIGS. 2A and 2B together are a schematic diagram of a control circuit for an implantable hyperthermia system including an internal or implanted system portion and the external portion for coupling to the internal portion;

Figure 1:
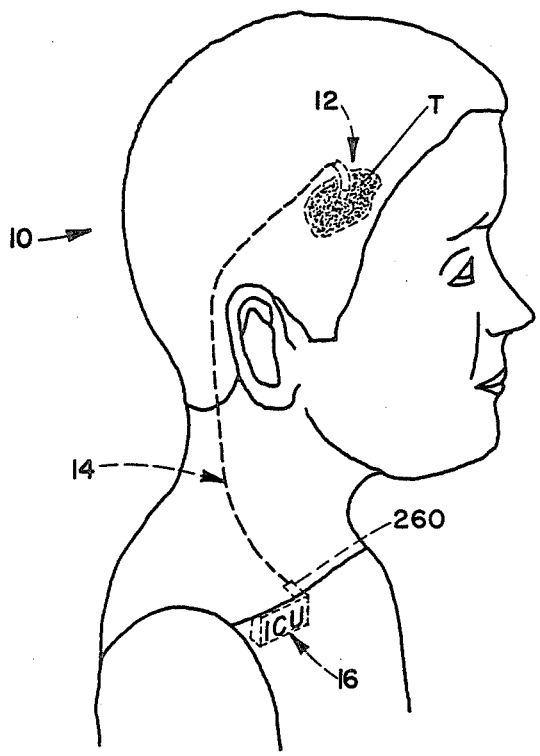

Referring to the drawings more particularly by reference numbers, number 10 in FIG. 1 refers to the head and upper body portion of a patient equipped with an implantable system constructed according to the present invention. The system includes a probe 12 which is shown imbedded in the head of the patient in position to extend from the surface or cranium of the head inwardly into a tumor T to be treated. A cable 14 is connected between the probe 12 and the internal control unit 16. The probe 12, the cable 14, and the internal control unit 16 are all surgically implanted in the body of the patient beneath the surface of the skin so that there is no protruding portion of the system which extends through or pierces the skin surface. This is important to the prolonged functional operation of the system since having the internal portions of the system completely implanted substantially reduces or eliminates the chances for infection and it is therefore expected that the internal system can remain in place for an extended period of time without any further surgical procedure being required. The details of the probe 12 and the internal control unit 16 will be described more in detail in connection with FIGS. 2A and 3.

Figure 2A:
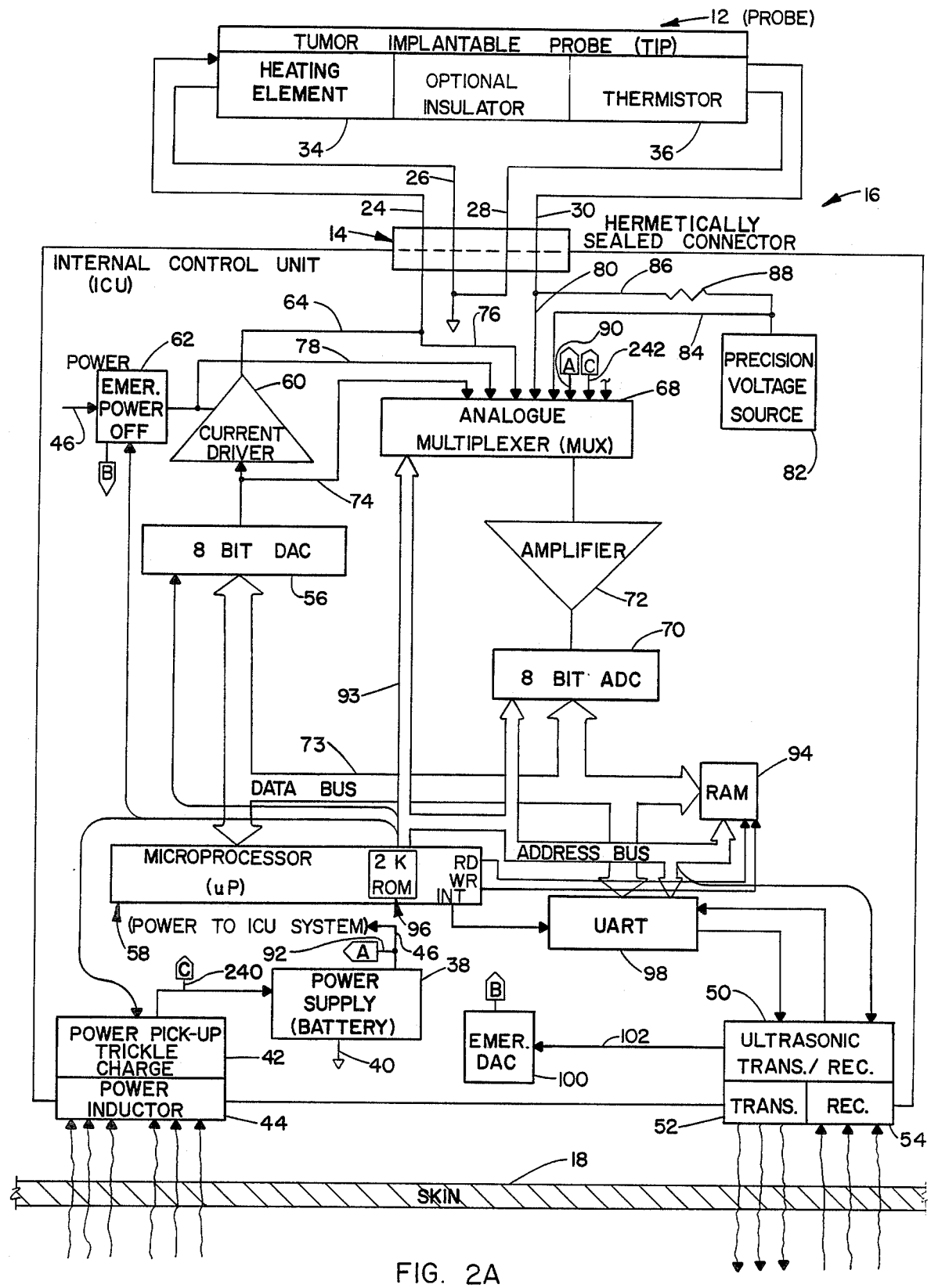
Figure 2B:
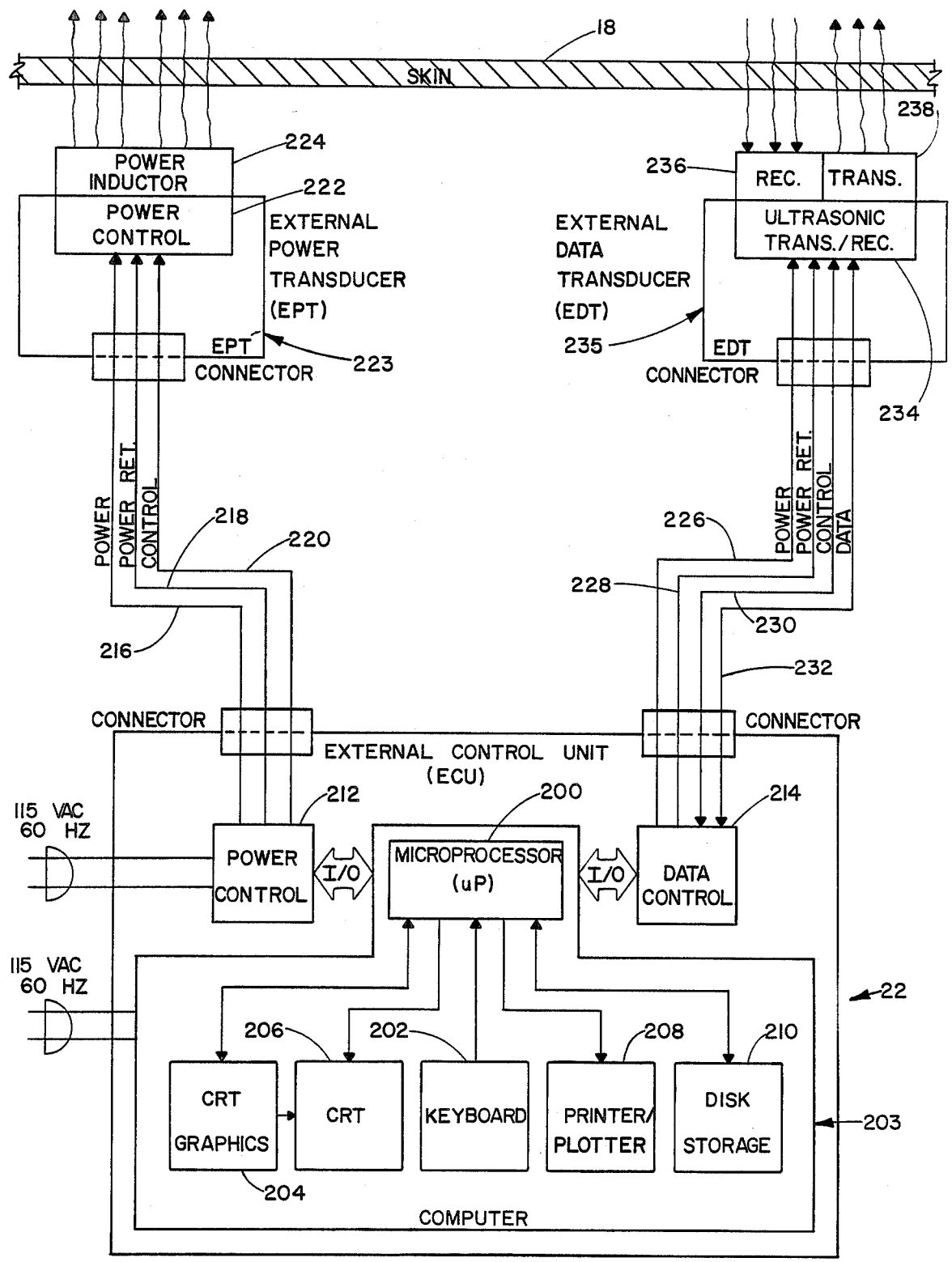

In FIGS. 2A and 2B, the skin 18 of the patient is shown positioned between the internal control unit 16 and an external control unit 22. The internal control unit 16 is shown coupled by leads 24, 26, 28, and 30 which are in the cable 14 to control elements located in the probe 12 including one or more heater elements 34 and one or more heat sensitive elements or thermistors 36. The probe 12, including the elements 34 and 36, and the internal control unit 16, are all surgically implanted under the skin of the patient so that nothing pierces or extends through the skin to cause infection or other problems. As stated, this is an important advantage of the present system. The internal control unit 16 includes means for controlling the application of electrical energy to the heater element or elements 34 according to some predetermined program or instructions established in the internal control unit and changed from time to time by the external unit 22 as will be described. The internal control unit 16 also has connections with the thermistor or thermistors 36 located on or adjacent to the probe at locations such that the thermistors are able to sense the temperature in the treatment area or tumor and provide outputs which can be used to evaluate and assess the effect of the treatment to enable modifying the treatment including the amount of heat generated by the heater element 34 as required to maintain some internal temperature condition for treatment purposes. For example, if the temperature of the tumor as sensed decreases then additional energy may need to be applied to the heater element 34 to maintain the temperature in the tumor at some desired level and for some desired time period or periods.

The heater elements 34 are preferably selected to be non-inductive, to have relatively low temperature coefficients and to be resistive type elements. The heaters should be able to increase the temperature of the surrounding tissue from normal body temperature of about 37° C. to a maximum temperature adjacent thereto of about 45° C. The heaters 34 should also be able to withstand repeated exposure to radiation without any degradation in performance characteristics such as degradation in resistance, temperature coefficient, heat capacity and/or heat dissipation constant. For a typical probe construction the heater elements should also be as small as practical, and a typical size is in the order of 2 millimeters in diameter and 6 millimeters in length. Such devices are available commercially.

Referring to FIG. 2A the internal control unit 16 includes a power supply 38, grounded at 40 and shown connected to a power pick-up trickle charge circuit 42 which in turn is connected to a power inductor coil 44. The inductor coil 44 is preferably located on the unit 16 as near as possible to the surface of the skin 18 so that external means can be closely coupled thereto when it is necessary to recharge or trickle charge the power supply 38. The power supply 38 may include a rechargeable battery or some other similar rechargeable energy source. The power supply 38 has an output connection 46 which is the main power lead used to supply energy for the internal control unit including for operating the heater and thermistor elements 34 and 36.

The internal control unit (ICU) 16 is the portion of the system that controls the temperature generated by the heater element 34 as programmed internally by means of the external control unit (ECU) 22. The internal control unit 16 also includes ultrasonic transmit/receive means (transceiver) 50 which include transmitting portion 52 used to transmit information for receipt by the external control unit 22, and a receiver portion 54 which receives information transmitted by the external control unit 22 for various purposes including programming and reprogramming the internal control unit and controlling the transmissions of information between the units. The internal control unit includes a digital to analogue converter (DAC) circuit 56 which converts 8-bit binary parallel words from the output of an internal microprocessor (uP) 58 to current outputs which are used to energize the heater 34 to produce the amount of heat that is desired. The output of the 8-bit DAC 56 is applied through a current driver circuit 60 which may be an emitter follower circuit that receives power from the power supply 38 by way of emergency power-off circuit 62 connected thereto, as shown. The output of the current driver circuit 60 is a voltage that is applied to the non-grounded side of the heater element 34 by leads 64 and 24. The same output applied to the heater 34 is also applied as an input to an analogue multiplexer (MUX) circuit 68. The analogue multiplexer 68, under control of the microprocessor 58, is constructed and connected so as to be able to select and monitor various conditions throughout the internal control unit including the voltage on the heater element 34, the voltage on the thermistor or heat sensor 36, as well as other circuit conditions, and it converts the signals or responses being monitored to a digital format by means of an 8-bit analogue to digital converter (ADC) 70 by way of amplifier circuit 72. The signals thus converted are applied to the data bus 73 for entry into the microprocessor 58 and other circuit components. The analogue multiplexer 68 has other input connections from various locations in the circuit including an input connection from the output of the 8-bit digital to analogue converter 56 on lead 74, an input from the output of the current driver 60 on leads 64 and 76, an input from the output of the emergency power-off component 62 on lead 78, an input from the non-grounded side of the thermistor 36 on leads 30 and 80, and inputs from a precision voltage source 82 on leads 84, 86 and 80. The precision voltage source 82 is used in connection with the calibration of the thermistor 36. The lead 86 from the source 82 includes a biasing resistor 88. The analogue multiplexer 68 also has a power input connection on lead 90 which is connected to output lead 92 on the power supply 38. The analogue multiplexer 68 is controlled from the microprocessor 58 and from other circuit connections by signals present on address bus 93 whereby the analogue multiplexer 68 can, among other things, maintain accuracy of the system even if some of the circuit parameters drift out of specification by automatically compensating for such errors. As a result the need for further surgery to manually adjust or replace implanted components is substantially reduced.

The microprocessor 58, as indicated, is the portion of the internal control unit 16 that controls all of the various functions thereof including also the functions of communicating with the external control unit 22. The microprocessor 58 has control and other connections including data and address connections to a 1024 bit random access memory (RAM) 94 which memory is programmable from the external control unit 22. When programmed the RAM 94 will enable a patient equipped with the subject internal control unit 16 to be able to undergo hyperthermia treatment while away from or out of communication with the external control unit 22. This is an important feature of the present device because it means that therapy can proceed continuously, reliably, safely, and in a precisely controllable manner for extended periods of time without constant attention thereby enabling the patient to maintain a fairly normal lifestyle even while undergoing treatment. The RAM 94 also converts data from the MUX 68 for subsequent transmittal to the external control unit.

Other portions of the internal control unit include a 2-K read only memory (ROM) 96 which is shown as part of the microprocessor 58 itself, an universal asynchronous receive/transmit circuit (UART) 98 which is provided to couple the microprocessor 58 as well as other portions of the internal control unit 16 to the ultrasonic transmit/receive circuit 50 which converts signals between the internal and external control units. The internal control unit 16 may include an emergency digital to analogue converter (DAC) 100 which can be connected to the ultrasonic transceiver 50 by lead 102 and connected to the power supply by way of the emergency power-off circuit 62. In addition, the internal control circuit 16 includes various circuit connections including the data bus 73 described above which has connections between the 8-bit DAC 56, the microprocessor 58, the 8-bit analogue to digital converter (ADC) 70, the RAM 94, and the UART 98. A second group of interconnections identified as the address bus 93 which provides other connections between the microprocessor 58, the analogue multiplexer (MUX) 68, the 8-bit (ADC) 70, the RAM 94, the UART 98, the 8-bit (DAC) 56, the emergency power-off circuit 62 and the trickle charge circuit 42. The circuit elements included in the internal control unit 16 may be constructed using conventional technology, and their operations will be described more in detail in connection with the flow charts shown in FIGS. 7A and 7B. In general, however, the internal control unit operates to regulate the amount, frequency, and time duration of the heat applied by the heater element 34 to establish and maintain a desired tumor temperature all of which functions depend upon the programming of the internal control unit as controlled and modified by the external controls and the tumor temperature as sensed by the temperature sensors or thermistors 36. If it is desired to maintain a predetermined temperature in the tumor the circuit will be programmed to energize the heater element 34 to some desired level to produce sufficient heat to reach the desired tumor treatment temperature. Thereafter, the amount of heat generated is determined by the voltage across the heater element 34 and will be adjusted manually or automatically. The amount of adjustment necessary will depend on the difference between normal body temperature and the desired temperature, the duration of time heat is applied, the frequency of the application of heat, changes in the temperature of the tumor as sensed by the thermistor 36, and changes that may occur in the tumor itself as the treatment proceeds. All of these and other factors can be programmed into the circuit. The amount of heat generated by the heater at any time will depend on the output word of the 8-bit DAC 56 operating through the current driver 60 as this output controls the voltage across the heater element and therefore the current flow therethrough.

The external control unit 22 shown in FIG. 2B includes the hardware and associated software necessary to effect clinical analysis of the data received from the internal control unit 16 and data from other sources that may be required. The external control unit has its own microprocessor (uP) 200 which is programmed from keyboard 202 and is part of an associated computer 203. The microprocessor 200 has outputs that feed a cathode ray tube graphics circuit 204, a cathode ray tube 206 which may have a connection from the graphics circuit 204, a printer/plotter 208 if need be and possibly a disc storage device 210. The elements 204, 206, 208 and 210 are optional depending upon the needs and sophistication of the system with which the subject device is to be used and the needs of the operator. The microprocessor 200 also has input/output connections to a power control circuit 212 and to a data control circuit 214. The main external power control circuit 212 has output leads 216, 218 and 220 which are connected to another power control circuit 222 which is part of an external power transducer (EPT) 223 and is connected to an external power inductor 224 which when used is positioned against the skin 18 adjacent to the internal power inductor 44. This is done when it is desired to trickle charge the internal power supply 38 as aforesaid. The lead 216 is the power lead, the lead 218 is the power return lead, and the lead 220 is the power control lead on which signals appear which control the charging of the power supply 38. The main external power control circuit 212 receives input power from a conventional source such as through a wall outlet and supplies power to the power control 222 and from there to the inductor 224 which is coupled to the inductor 44 to recharge the power supply battery 38 in the internal control unit 16. The use of electromagnetic coupling between an implanted power source 38 and an external power transducer through the skin as a means for maintaining energy for operating an implanted system such as disclosed herein has not been used before so far as known. Such a rechargeable supply is very important to the present system because not only is it expected that relatively large amounts of power may be required to generate the heat necessary to raise and maintain the tumor temperature at some desired level but it may be necessary to maintain these conditions for protracted periods to meet the needs of the treatment. A rechargeable power supply affords this possibility. It is also possible and contemplated to couple the external power transducer 223 to the internal power means during treatment so that at least some of the power to operate the internal control unit will be maintained and supported more directly by the external power supply particularly during periods of greatest demand. In some cases the required power may come through coupling means directly from the external power source to the heater or through some combination of external and internal power.

In like manner, the data control circuit 214 has connections on lead 226 which is a power lead, lead 228 which is a power return lead, lead 230 which is an input/output control lead, and lead 232 which is an input/output data lead to an ultrasonic transmitter/receiver means 234. The means 234 are included in an external data transducer 235 which is connected to external receiver 236 for coupling to the internal transmitter 52 of the internal unit 16, and to external transmitter 238 for coupling to the internal receiver 54. It can therefore be seen that the external power control portion 222 can be coupled to the internal power pick-up 42 through inductors 224 and 44 for charging and recharging the internal power supply 38, and simultaneously the ultrasonic transmit/receive means 234 including the associated receiver means 236 and transmitter means 238 can be coupled to the internal transmit/receive means 50 which includes transmitting portion 52 and receiving portion 54. These latter means, when coupled, can exchange data and other information between the internal and external units. In this way the internal unit can be programmed from time to time as desired, and the information gathered by the internal unit can be evaluated from time to time in the external control unit by computer means connected thereto and controlled by suitable software. The computer, using updated information from the patient as the treatment proceeds, or from time to time based on the patient's particular treatment program, can reprogram the internal control unit according to the changing needs of the patient. When exchanging data between the units, and especially when charging the power supply, it is greatly preferred that the distance between the power inductors 44 and 224 be as close as possible to minimize power loss. It is also preferred that the location of the internal and external transmission and receiving means associated with the transfer of data be relatively close to avoid transmission loss and errors. It may be desirable in some cases to mark the skin at the locations of the means 44, 52, and 54 as an aid in more accurately locating the corresponding external members to be coupled thereto especially if the units are to be separated from each other. This can also be done automatically using the computer program in the ECU in conjunction with monitoring the trickle charge circuit by way of the analogue multiplexer 68, see connection leads 240 and 242 in FIG. 2A. To this end it is preferred that all of the internal and all of the external coupling means be mounted on respective housings that facilitate proper orientation during use.

Figure 3:
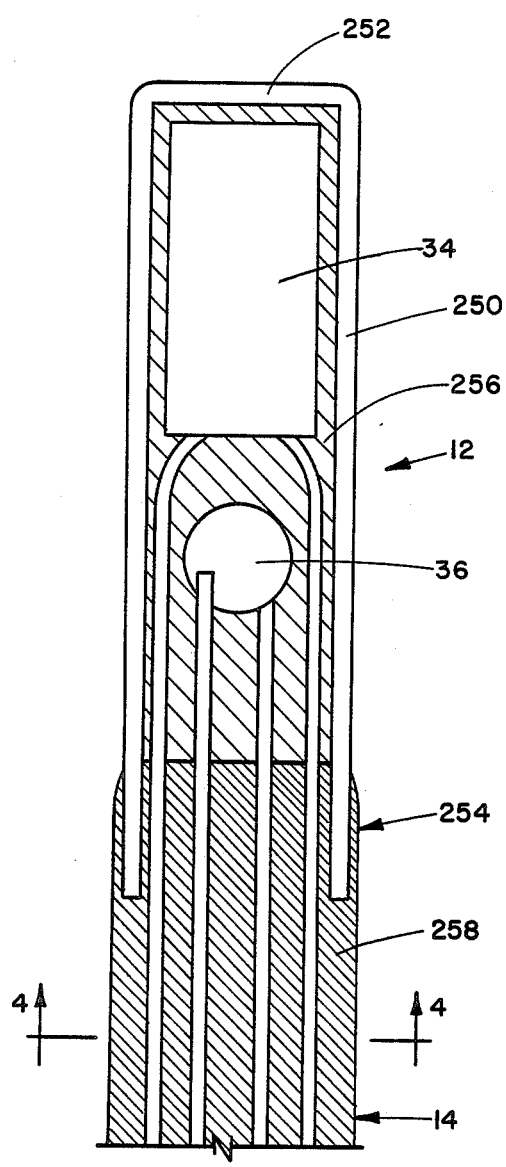
FIG. 3 is an enlarged cross-sectional view through a single element probe with a portion of cable attached thereto for use with the present device.

FIG. 3 is an enlarged cross-sectional view of a typical probe 12 of the type that might be used to treat a brain tumor using the present invention. The probe 12 is shown including an elongated tubular wall 250 closed by wall portion 252 at one end and constructed of a relatively thin inert substance such as 316L, FDA Approved stainless steel, certain plastics or glass. The diameter of the tube 12 should be as small as practical to accomodate whatever number of heater elements 34 and sensors 36 are required and the wall 250 should also be as thin as possible. A probe diameter in the range of about 1/10 of an inch or 2 millimeters is a good choice and the thickness of the wall 250 should be in a range of about 1/100 of an inch. These ranges can vary as much as several hundred percent or more. The length of the probe selected for a particular application should be selected to be long enough to extend from the cranium to the tumor treatment area. The inserted end portion of the probe may optionally be tapered at its end to facilitate its insertion in place with minimal damage to the surrounding tissue and with minimal surgical preparation. The inserted probe end wall 252 is shown as being integral with the side wall 250 and the probe edges are preferably rounded as shown. The opposite end of the probe 12 is shown connected to the cable 14 at 254 such that the cable forms a flexible continuation of the probe. The cable is preferably formed of a material such as an elastomer, and the cable 14 should be flexible enough so that it can be laid along the outer surface of the cranium, under the skin, without producing an unsightly or irritating surface condition. The heater 34 and the sensor 36 are shown embedded in a thermo-conductive electrically insulative material 256 such as a highly thermoconductive epoxy and the cable 14 is formed of an elastomer material 258. A good selection of a highly thermo-conductive epoxy for the heat conductive material is Castall 343AB, and a typical elastomer for the cable material 258 is Dow Corning elastomer MDX-4-4210.

The internal control unit will typically be implanted under the clavicle or collar bone where there is sufficient space and where there is least discomfort to the patient. The probe 12 should be constructed to thermally and electrically isolate the heater element 34 from the heat sensor 36, and this can be done by separating them from each other as much as possible and by providing insulation therebetween, if desired. The material 256 serves this purpose to a limited extent, and it is contemplated to include other means to thermally insulate the members 34 and 36 from direct or close exposure to each other.

As indicated above, the heater element 34 and the thermistor 36 should be as small as practicable, and the selection of the thermistor for use on the subject device should take into account its impedance which should be relatively high, and it should have high stability characteristics with a negative temperature coefficient. Known glass bead type thermistors have these characteristics. A typical thermistor for use on the subject device will be approximately 2 millimeters in diameter and can have a length that may vary from a few millimeters to a centimeter or longer.

Figure 4:
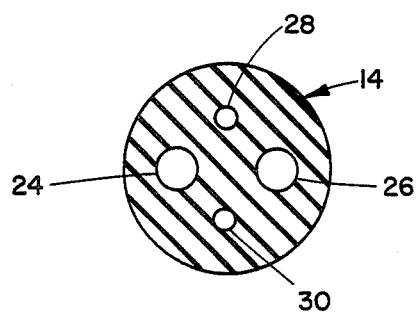
FIG. 4 is a cross-sectional view taken on line 4—4 of FIG. 3.

The cable 14 which is connected between the probe 12 including the heater element, the thermistor and the internal control unit should be as small in diameter as possible and preferably should be relatively flexible so that it will not interfer with normal body movements and will not be uncomfortable or unsightly to the patient even when implanted under the skin on the skull. The cable 14 will contain a connector 260 (FIG. 1) or plug at the end opposite from the probe 12 which mates with and makes a sealed attachment with plug means on the housing of the internal control unit. A typical cable for use on the present device is shown in cross-section in FIG. 4 and includes the two heater wires 24 and 26 and the two thermistor wires 28 and 30. The wires 24 and 26 are larger in diameter than the wires 28 and 30 because they must be able to carry sufficient current to produce the amount of heat required and programmed into the system. A typical wire size for the heater wires 24 and 26 is approximately 26 AWG solid, possibly silver wire, and a typical wire size for the thermistor wires 28 and 30 is 32 AWG solid wire. The four wires 24–30 will be insulated and will be separated from each other and from the body environment by being positioned in the single molded plastic flexible cable formed of an elastomer 258 or like material, as stated. A cable having a diameter typically in a range around approximately 1.5 millimeters is preferred. FIG. 4 shows one preferred arrangement for the wires 24–30 in the four wire cable 14. The particular arrangement of the wires 24–30 in FIG. 4 are for illustrative purposes and may be differently located in the cable 14 depending on their number and size.

The connections between the cable 14, the probe 12 and the internal control unit 16 should be made by hermetically sealed locking members or connections to prevent the intrusion of corrosive body fluids. The connections will usually be made during surgery when the system is implanted although in some situations if the cable length can be accurately determined in advance of surgery the connections can be made ahead of time to save the time and effort of the surgeon. If the connections are made ahead of time they can also be further protected by heat treating or the application of an additional sealer.

Figure 5:
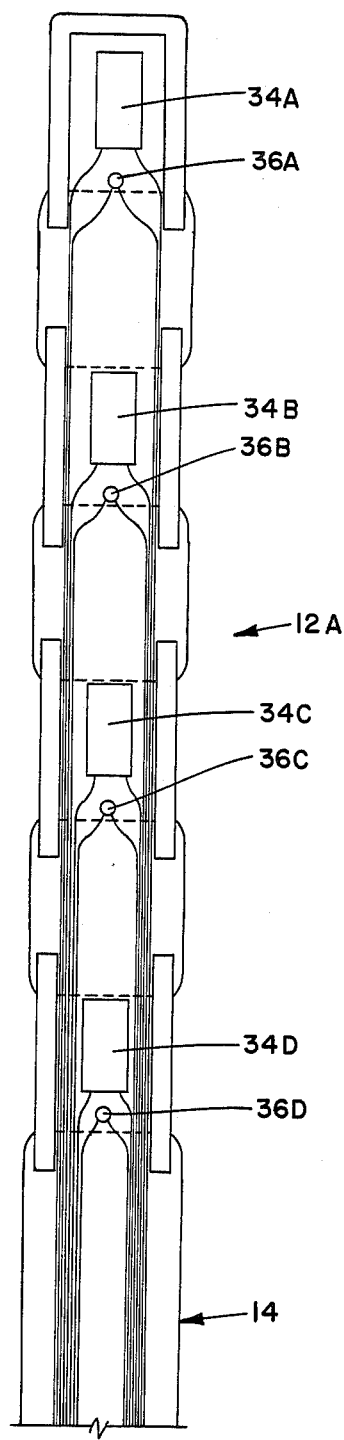
FIG. 5 is an enlarged cross-sectional view through a multiple element probe with a portion of cable attached thereto for use with the present device.

The preferred form of the probe 12 is the form 12A shown in FIG. 5 wherein the probe is an elongated member and has a plurality of spaced heater elements 34A–D and a plurality of spaced sensor elements 36A–D. In the preferred form the heater elements and sensors are alternately spaced along the device and the number of heater elements and sensors can be varied as required depending upon circumstances such as the size of the tumor and the distance over which heat is to be applied and over which the sensors are to monitor the tissue temperature. Each of the heaters 34A–D has a pair of electric connections to it as does each of the sensors 36A–D. However, because of the arrangement of the elements in the probe 12A it is necessary to have the connections for most, if not all, of the elements extend adjacent to the periphery of the probe in order to pass by the other elements. In the construction as shown this means there must be provisions for 16 wires extending between the elements and the internal control unit. This also means that the internal control unit may have separate means to power each of the different heaters and separate means to receive and store the different sensor readings.

In the usual situation only a selected one of the heater elements 34A–D will be energized at one time for treatment purposes, and selected ones of the sensors will provide temperature outputs for evaluation and other purposes. This means that there will be a relatively large space between the sensors that are being read and the heater that is being energized and the sensors being read will be relatively little affected by direct heat from the energized heater elements. This also means that the sensor temperatures being monitored or read will be more influenced by the temperature of the tissue adjacent the sensors than by the heater. Which of the heater elements is to be energized and which of the sensors are to be monitored for outputs will depend upon the programming of the systems, and the programming, which is done externally by the external computer 203, can selectively energize the several different heater elements in any desired order to generate heat at different locations along the probe, and in some cases it may even be desireable to energize more than one heater element at the same time although this is usually avoided to minimize the current drainage of the internal battery source. In one experimental application wherein a probe was placed in a rabbit's brain the current required to operate the one heater was on the order of 43.0 milliamps. If more than one heater is energized obviously the current requirements will increase correspondingly. It is also possible to use a probe having one heater element and one sensor as shown in FIG. 3, but this is usually not desired since in such a construction the sensor element or thermistor may be unduly influenced by the temperature generated by the heater element in relation to the temperature of the surrounding tissue.

It is also contemplated for experimental purposes to implant a probe extending into the tumor to be treated, as aforesaid, but to have the cable 14 extend through the patient's skin to the external control unit thereby making it possible to combine the internal and external control means into one unit. This will afford an easier way to operate the system and will reduce the surgical procedures necessary and obviate other needs for an internal power source. While such a system may afford an easier and possibly more reliable way to apply treatments, it is usually not the preferred form since it ties the patient to the controls and it also results in a location on the skin where infection can more easily start. However, for some cases, and for experimental applications such a system may have advantages.

Figure 6:
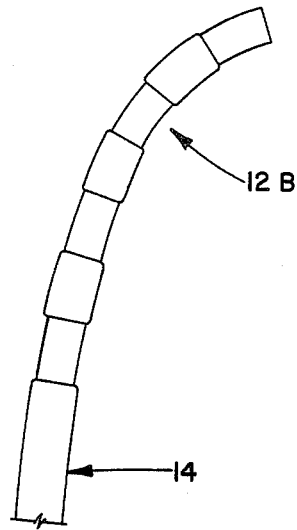
FIG. 6 is a side view of the probe and cable portion of FIG. 5 but shown in a non-linear configuration.

In addition, it is contemplated to connect and control the heaters and sensors in more than one probe from the same control unit as in a situation where it is desired to generate heat in more than one tumor or tumor location at the same time. Furthermore, the probe 12A can be formed to be other than straight as shown by the probe 12B in FIG. 6. There are thus many arrangements, shapes, and styles of probes that can be used, including more than one type of probe on a single patient, and the present invention offers the possibility of selecting different probes and probe arrangements to treat different tumors. This gives the doctor many more options for tumor treatment of cancer patients, and it does so using a device that produces minimal surgical damage to the patient as when the probe is inserted and removed. The path for inserting the probe can be prepared in advance if desired using a relatively pointed surgical instrument and the depth of penetration of the probe can be determined from data obtained using known means to accurately locate the tumor.

The ultrasonic data transceivers 50 and 234 provide the data link between the internal control unit and the external control unit. For example, the transceiver 234 in the external control unit can convert incoming serial digital data from the data control circuit 214 into bursts of ultrasonic energy to be transmitted through the skin to the transceiver 50 in the internal control unit. The transceiver 50 will then convert the data back to serial digital data that is compatible with the UART 98 in the internal control unit for use by the internal microprocessor 58 to control the various functions of the internal control unit including the programming. The RAM 94, as stated, is programmable in this fashion by the external control unit and is the portion of the internal control unit that will enable a patient to undergo hyperthermia treatment while away from the external control unit. This is an important advantage of the present system. In a similar manner, the transceiver 50 in the internal control unit can convert incoming serial data from the UART 98 into bursts of ultrasonic energy that will be received by the transceiver 234 in the external control unit and there converted back to serial digital data that will be sent to the data control circuit 214 for processing by the computer.

The external control unit, as explained, is that portion of the system that contains the operational program including the keyboard and the software for the entire system. The external control unit generally will also include a computer such as the personal computer 203, a power control circuit portion 212, a data control portion 214, an external power transducer 223 and an external data transducer 235 all connected as shown in FIG. 2B. The hardware and software in the external control unit will effect all the clinical analysis of the data including clinical analysis of information and data received from the internal control unit, and depending on the program and data available, will make decisions as to how the therapy will proceed. The computer 203 is part of the external control unit 22 and includes the microprocessor 200 and the keyboard 202 and may also include the graphics module 204, the cathode ray tube 206, the printer/plotter 208, and the disc storage 210. These may all be off-the-shelf items. In addition to the features indicated, the computer will also contain the necessary peripherals and software to effect any clinical analyses that may be required. The external power control circuit 212 interfaces with the computer 203 and contains the necessary decoding circuitry so that the current flow in the power inductor 224 will be turned on and off under control of the operation program contained in the computer and this will also enable the operator to start and stop the trickle charge or power transfer from the external to the internal units without removing and/or repositioning the power inductor 224 and the members 236 and 238 even during prolonged periods of clinical testing. The external control circuit will also contain the necessary decoding circuitry to control the mode of operation and the sequence of the transmissions and receptions between the internal and external control units. Necessary buffer circuitry may also be required to enable receipt and transmittal of serial digital data from one unit to the other.

The external power transducer 223 which includes the power control 222 and is provided to induce current flow into the power pick-up 42 by coupling through the skin should preferably be as light weight as possible and should be easily positioned against the outside surface of the skin so that the inductor 224 will be closely adjacent to the internal inductor 44. It may be desirable to provide a monitoring routine as an aid to properly positioning the external power inductor 224 to maximize the current flow into the power pick-up 42 by maximizing the coupling to increase the power transfer efficiency.

The external data transducer 235 which includes the ultrasonic transmit/receive means 234 is the portion of the external control unit that converts incoming serial digital data from the computer 203 into bursts of ultrasonic energy for transmission to the ultrasonic receiver 54. The external data transducer 235 operates to convert signals received from the internal control unit to serial digital form for sending to the computer 203. The ultrasonic transceiver 50 serves somewhat similar functions in the internal control unit 16.

A description of the software is also necessary to a complete understanding of the present invention. The software is associated with the computer means in the external control portion of the subject device and is used to analyze information received from the internal control unit and to provide information for programming the internal control unit according to its analysis and assessment and according to the instructions it receives by operation of the keyboard. The information gathered can also be used for diagnostic purposes independently of the heater means if desired. For example, the data available from the sensors can be used to evaluate a condition prior to or following a treatment to determine if treatment is necessary or if a treatment has been successful. The various functions of the software will be described in connection with a typical treatment situation and reference should be made during this description to the flow charts shown in FIGS. 7A and 7B. It will also be assumed in this description that the internal control unit has been implanted in the patient and is working properly. Under these circumstances when power is first applied to the external control unit, the software will immediately go into an initialization testing routine. The purpose of this routine is to verify the proper operation of the system and to perform some basic testing before reaching a safe-to-continue condition. If, during this period, any failure is detected, indicating a dangerous condition to the patient as determined by monitoring certain circuits, all power will be removed from the system immediately. Such failures typically include such things as runaway or excessive heater current, an open sensor circuit, a shorted power supply, a failure of the transmission or receiver means, a failure of the data handling means, or a failure of the power coupling means. Under these conditions no application of current will be applied to the heater element 34. On the other hand, if the tests indicate that the system is operating normally, a System Normal condition will be reached and it will then be necessary for the operator to select between the automatic or the manual mode of operation. The selection made will determine the course of future operations.

If the operator selects a manual mode of operation by operating an appropriate key on the keyboard, all operations and functions of the system will be under control of the operator and the operator will then have to constantly monitor all activity occurring within the system.

The operator will be aided in this by a display on the cathode ray tube 206 and/or by other means in the computer. A record of the operations may be made on the printer 208 and stored in the disc storage 210. If the manual mode of operation is selected the operator must then select the following 7 parameters before proceeding, namely;

1. An 8-bit digital to analogue converter (DAC) word. The selection of this binary word will determine the temperature that will be generated in the heater element 34 and hence in the tumor being treated. The selection of a particular 8-bit word will cause a search operation to take place in a look-up table in order to produce an appropriate temperature representation or constant. The system will stay at the constant selected to represent the desired temperature for the duration of the test.

2. The operator will select a time for the temperature that has been selected to be applied. This time will be selected by operating the appropriate key on the keyboard 202 associated with the computer 203.

3. The operator will select an address for applying to the analogue multiplexer 68 by operating another key on the keyboard 202, and this will allow the operator to monitor any or all of the connected internal test points in the internal control circuit to assure proper operation. The multiplexer 68 is shown having 8 such input connections which are connected to various portions of the circuit. Some of these 8 connections are not used in the embodiment shown in FIG. 2A.

4. The operator will operate another key which will determine the frequency that sample data will be read from the analogue multiplexer 68.

5. Another key on the keyboard 202 will be depressed to cause a trickle charge to be applied to the internal power supply or battery 38 as required. The frequency at which this is necessary will depend upon how much heat is generated by the heater element and the characteristics of the battery in the internal control unit. It is also contemplated that the internal control unit may include means for responding to the charge remaining on the battery 38 which, depending on the type of battery used, may include means to tell when the battery charge has fallen far enough to indicate a potentially dangerous condition or a condition that indicates recharging is necessary.

6. Another required input is produced by operation of a key on the keyboard 202 to enable the internal RAM 94 to store data it receives from the analogue multiplexer 68. The data thus stored can be later transmitted back to the external control unit for evaluation.

7. The operator must also determine where he wants certain of the data being monitored to go. For example, he may feed the data to the disc 210 for storage, he may feed it to the printer 208, he may feed it to the graphics display 204, and he may instruct the unit to display the information on the cathode ray tube 206. This will depend upon the available equipment in the computer portions of the external control unit.

All of the above operations and selections are made in the manual mode and when the internal and external units are coupled together as described above with the inductors 44 and 224 adjacent one another, and with the transmitter and receiver portions 52 and 54 adjacent to the receiver and transmitter portions 236 and 238 respectively.

After the above selections have been made and the operator is satisfied with the results and tests, the system will require a start command to begin actual execution of a treatment. When the RAM 94 is enabled, a command will be sent from the external control unit 22 to divert all of the analogue multiplexer 68 outputs for entry into the internal control unit RAM 94. If a trickle charge operation is required a command will also be sent to the external power transducer 223 to initiate that operation. Also, if treatment is called for, the selected 8-bit binary word or byte will be sent to the digital to analogue converter 56 for applying the appropriate voltage across the heater element or elements 34. The analogue multiplexer 68 sample rate will also be checked to see if a polling sequence is required, and if not a countdown will take place and a check made to see if the allotted time has expired. If the allotted time has expired the DAC 56 input is removed and a Time Expired display will appear on the cathode ray tube 206. The system will then await further inputs from the operator. If the allotted treatment time has not expired the program will loop and continue to see if a polling sequence should be initiated. When this happens a polling routine will read in those multiplexer inputs that were initially selected by the operator as aforesaid. The 8-bit output of the analogue to digital converter 70 will be sent to the external control unit 22 (or to the RAM 94) to be stored and/or displayed to the operator. This process will continue to repeat itself until the time has expired. This will be apparent by referring to the flow charts in FIGS. 7A and 7B.

If the operator selected the Automatic Mode instead of the manual mode he must then select 6 parameters rather than 7 before proceeding. The parameters that must be selected in the automatic mode are:

1. Final Temperature—this parameter may be specified in °C. or any other desired temperature and is the tumor temperature that is desired to be reached as determined by the output of the sensor or sensors 36.

2. Time To Reach—this input parameter forces the software to select the proper algorithm required to raise the temperature of the heater element 34 sufficiently to reach the required tumor temperature in the requested time.

3. Time Applied—once the desired temperature in the tumor has been reached this parameter, as selected, establishes the length of time that the desired tumor temperature will be maintained.

4. Number of Cycles Required—this parameter will establish and control whether more than one cycle of treatment is required and will further specify and control the number of treatment cycles that will be produced.

5. Time Between Cycles—this parameter allows for more treatment periods during which the heater elements are deenergized and a return toward ambient conditions in the tumor will result.

6. Data Peripherals—this parameter, controls what data will be stored in and/or displayed for the operator.

After the selection parameters for the automatic mode have been completed, a start command is required to begin the execution. The algorithm routine that was selected will then take over and determine how much power is to be applied to the heater element to produce the desired tumor temperature. This decision will be based mainly on the desired temperature to be reached as indicated by the sensor and on the rate of heat application required to achieve the desired temperature. Other factors affecting this include the characteristics of the tumor and the ability of the body to dissipate heat from the tumor. Once this decision is made in the algorithm routine an appropriate 8-bit command will be sent to the digital to analogue converter 56 for application of voltage to the heater element 34. The analogue multiplexer 68 will then be polled at appropriate time or times and data will be gathered, stored and analyzed, and this procedure will continue until the desired temperature as determined by the sensor or sensors 36 is reached. Once the desired tumor temperature is reached a countdown cycle may begin based on the desired time of application of heat and changes that will be made to the output of the digital to analogue converter 56 word to maintain a constant temperature condition as determined by the sensors 36. If more than one sensor 36 is used this may involve averaging the outputs of the sensors to determine the heater voltage to be applied. Once the time has expired for the application of heat treatment, the cycle parameters will be checked and if the cycle is finished a display indicating that the cycle is over will appear and the operator must then initiate further actions if more cycles are required or the treatment cycle can be terminated at that point. If more cycles are required a delay period will be counted down, the parameters will be reinitialized and another status display will be put on the cathode ray tube 206 to indicate the present condition to the operator. If called for, the complete cycle or a modified cycle of treatment will be restarted.

It is also possible using the present device to store instruction commands in the RAM 94 using the external control unit 22. If this is done the external control unit can be decoupled from the internal control unit 16 and the system can operate on its own internal power supply for an extended period of time depending upon the power storage capacity of the power supply 38 and the need to recheck the circuit parameters and introduce changes in the therapy, as required.

Figure 7A:
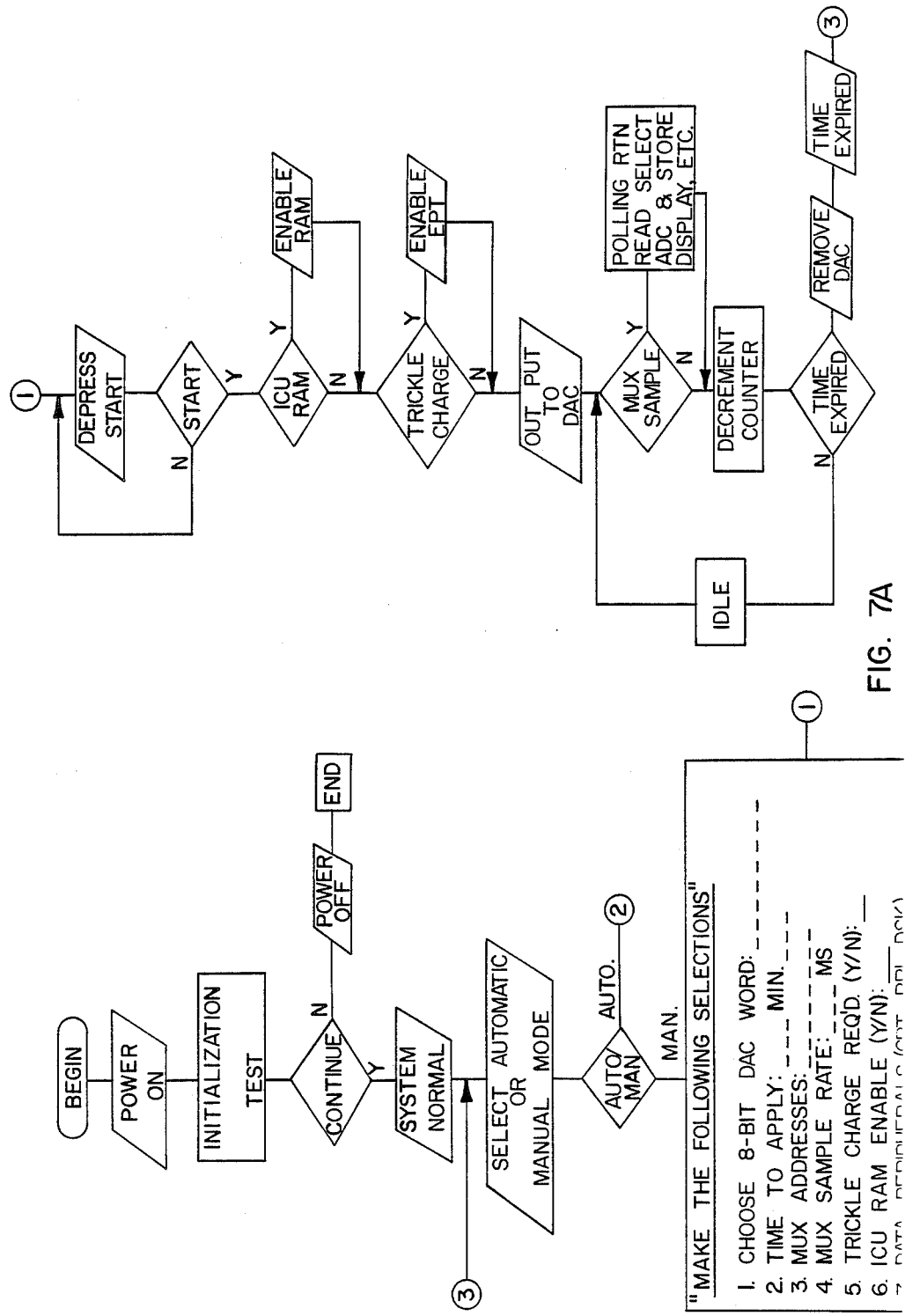
FIGS. 7A and 7B together are a flow chart for the systems shown in FIGS. 2A and 2B.
Figure 7B:
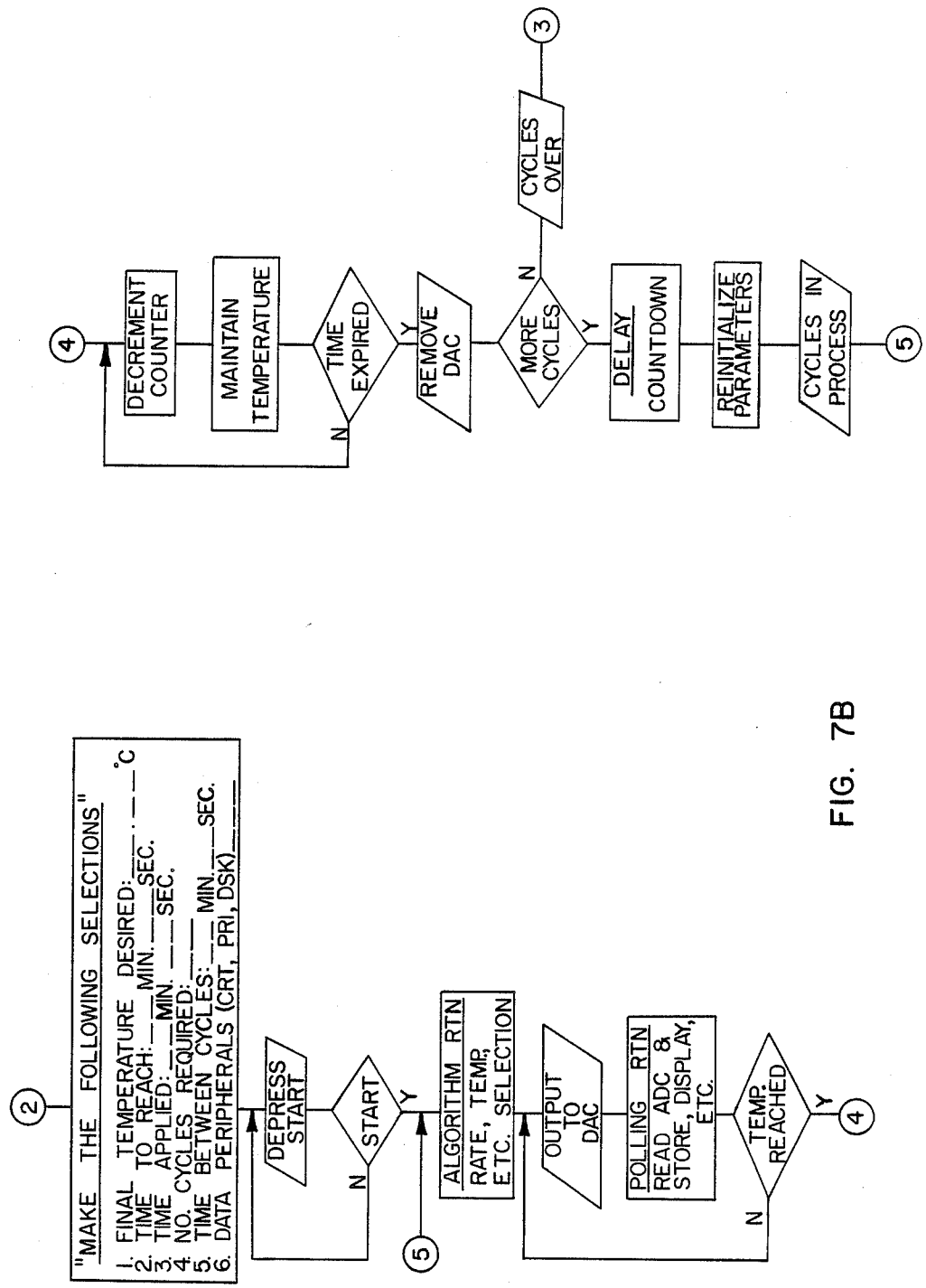

FIGS. 7A and 7B together form a flow chart for the subject device and should be considered in conjunction with the description of the manual and automatic operation as set forth above. The flow charts contain blocks which identify the various options available to the operator in the manual and automatic modes and it is believed that the above description will enable one skilled in the art to understand the flow charts.

The inputs to the multiplexer 68 may include various circuit connections including the circuit connections shown. These are used for test purposes and to verify certain circuit conditions as stated above. For example, such connections can be made to the ultrasonic transmit/receive means 50 to check the operating characteristics thereof. Similar connections could also be made to respond to the strength of the transmissions and receptions of information and this in turn could be used as a means for indicating whether the coupling between the internal and external units are properly made and are sufficient to support the necessary communications therebetween.

One of the most important aspects of the present invention resides in the fact that it provides means for introducing heat at a location that is within the tumor being treated and in such a way that all or substantially all of the heat that is generated in the heater element is generated in the tumor and radiates outwardly through the tumor and through the adjacent body portions from the heat source or heater element, and none or substantially none of the heat generated is therefore lost or ineffective. This means that the heat will be placed where it is most needed with little or no chance for damage to the surrounding tissue. This is not the case when radiation treatments are applied because the surrounding tissue and organs are exposed to the radiant energy which can cause damage thereto. In the case of brain tumors, radiation therapy frequently results in damage to brain tissue adjacent to the treatment area and this damage generally cannot be restored medically. This is not the case with the present device which does not produce any damaging radiation and concentrates the heat that is produced in the area where it is most needed. Furthermore, with the present system any desired number of probes with associated heaters and sensors can be used, the limiting factor usually being the capacity of the power supply to provide sufficient energy for all of the heaters. If a rechargeable internal power supply is used then the length of time that the device can be used when not coupled to an external source may be somewhat restricted. On the other hand, if power can be supplied to the heater elements by direct coupling with the external source then it may be possible to use any number of probes and associated heaters even for prolonged treatments. This can be an advantage in the treatment of large tumors and the treatment of more than one tumor at the same time using the same control units.

The present device can also be used with any number of heat sensors, and the sensors can be located at various positions in the tumor and if desired in the surrounding flesh and at various distances from the heater elements. This provides the possibility for determining the effectiveness of the heater element and the heat gradient in the areas being heated and it also provides the opportunity for observing the actual data changes in the heat dissipation rate which may take place as the treatment proceeds. For example, it is anticipated that the heat dissipation rate of a tumor will change as the treatment proceeds, and the ability of the circulatory system of the patient to carry away the heat during treatment may also change and this can be detected especially if multiple sensors are used. Also, if more than one sensor is used some formula or algorithm may be necessary to determine a mean average tumor temperature for control and evaluation purposes and also for the purposes of determining the temperature to be applied to the tumor by the heater elements. It can therefore be seen that the present device provides a powerful new modality or option for the treatment of body tumors and other organs, and particularly for the treatment of brain tumors which are difficult and dangerous to treat by other known means and which can be treated by the subject device with minimum damage and injury to the patient.

Thus there has been shown and described novel hyperthermia treatment means and method which fulfill all of the objects and advantages sought therefor. It will be apparent to those skilled in the art, however, that many changes, modifications, variations, and other uses and applications of the subject means and method are possible. All such changes, modifications, variations, and other uses and applications which do not depart from the spirit and scope of the invention are deemed to be covered by the invention which is limited only by the claims which follow.

What is claimed is:

1. A hyperthermia system for treating a cancerous brain tumor, comprising a system entirely implantable beneath the skin of the person being treated, said implantable system including a probe having opposite ends including a first end for extending into the brain tumor to be treated and a second end extendable therefrom to adjacent the surface of the skin, an electric heater element and a heat sensitive member mounted in the probe adjacent to the first end, and means for thermally insulating said heat sensitive member from said heater element, means operatively connected to the probe to select a predetermined temperature condition to be produced in the tumor, an electronic control unit under control of the means operable to select, and means operatively connecting the electronic control unit to the heater element and to the heat sensitive member, said electronic control unit including an energy source for the implantable system and means under control of the electronic control unit to apply energy from the energy source to the heater element to generate the selected predetermined temperature condition in the brain tumor to be treated adjacent to the probe, and closed-loop control means in the electronic control unit responsive to the condition of the heat sensitive member for controlling the application of energy to the heater element according to the difference between the selected predetermined and actual temperature conditions in the brain tumor being treated, the implant table system also including a programmable circuit including a memory circuit, and transmission and receiving means, said means operable to select, said electronic control unit and said programmable circuit being implantable in a remote location in the person's body, and an external control system having transmission and receiving means therein for coupling to the transmission and receiving means of the implantable system through the skin, said external control system including programmable means operable for programming the memory in the implantable system to establish the temperature conditions to be produced in the brain tumor being treated.

2. The hyperthermia system of claim 1 wherein the external control system includes means operable for energizing the heater element to produce and maintain the predetermined treatment temperature in the brain tumor being treated.

3. The hyperthermia system of claim 1 wherein the external control system includes means for selecting a predetermined time for maintaining the heater element energized to maintain the predetermined treatment temperature in the brain tumor being treated.

4. The hyperthermia system of claim 1 wherein the external control system includes means for establishing a predetermined frequency of treatment cycles when the heater element is energized.

5. The hyperthermia system of claim 1 wherein the energy source includes a rechargeable energy source, and means in the external control system operating through the transmission and receiving means when they are coupling the internal and external control systems for recharging the rechargeable energy source.

6. A hyperthermia system for treating a cancerous brain tumor, comprising a system entirely implantable beneath the skin of the person being treated, said implantable system including a probe having opposite ends including a first end for extending into the brain tumor to be treated and a second end extendable therefrom to adjacent the surface of the skin, an electric heater element and a heat sensitive member mounted in the probe adjacent to the first end, means operatively connected to the probe to select a predetermined temperature condition to be produced in the tumor, an electronic control unit under control of the means operable to select, and means operatively connecting the electronic control unit to the heater element and to the heat sensitive member, said electronic control unit including an energy source for the implantable system and means under control of the electronic control unit to apply energy from the energy source to the heater element to generate the selected predetermined temperature condition in the brain tumor to be treated adjacent to the probe, and closed-loop control means in the electronic control unit responsive to the condition of the heat sensitive member for controlling the application of energy to the heater element according to the difference between the selected predetermined and actual temperature conditions in the brain tumor being treated, the implantable system also including a programmable circuit including a memory circuit, and transmission and receiving means, said means operable to select, said electronic control unit and said programmable circuit being implantable in a remote location in the person's body, and an external control system having transmission and receiving means therein for coupling to the transmission and receiving means of the implantable system through the skin, said external control system including programmable means operable for programming the memory in the implantable system to establish the temperature conditions to be produced in the brain tumor being treated.

7. The hyperthermia system of claim 6 wherein the external control system includes means operable for energizing the heater element to produce and maintain the predetermined treatment temperature in the body tissue being treated.

8. The hyperthermia system of claim 6 wherein the external control system includes means for selecting a predetermined time for maintaining the heater element energized to maintain the predetermined treatment temperature in the body tissue being treated.

9. The hyperthermia system of claim 6 wherein the external control system includes means for establishing a predetermined frequency of treatment cycles when the heater element is energized.

10. The hyperthermia system of claim 6 wherein the energy source includes a rechargeable energy source, and means in the external control system operating through the transmission and receiving means when they are coupling the internal and external control systems for recharging the rechargeable energy source.

* * * * *